United States Patent
Yuan et al.

(10) Patent No.: US 7,019,034 B2
(45) Date of Patent: *Mar. 28, 2006

(54) COMPOSITIONS AND METHODS FOR REDUCING SERUM GLUCOSE AND TRIGLYCERIDE LEVELS IN DIABETIC MAMMALS

(75) Inventors: Yang-Dar Yuan, Irvine, CA (US); Richard L. Beard, Newport Beach, CA (US); Roshantha A. Chandraratna, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/738,808

(22) Filed: Dec. 17, 2003

(65) Prior Publication Data
US 2004/0147611 A1    Jul. 29, 2004

Related U.S. Application Data

(60) Provisional application No. 60/443,141, filed on Jan. 28, 2003.

(51) Int. Cl.
C07C 69/76 (2006.01)
A61K 31/19 (2006.01)
(52) U.S. Cl. .......................... 514/569; 560/56; 562/466
(58) Field of Classification Search ............... 560/56; 562/466; 514/532, 569
See application file for complete search history.

(56) References Cited

U.S. PATENT DOCUMENTS

| | | | |
|---|---|---|---|
| 5,455,265 A | 10/1995 | Chandraratna | |
| 5,801,253 A | 9/1998 | Klaus et al. | |
| 6,114,533 A | 9/2000 | Vuligonda et al. | |
| 6,759,547 B1 * | 7/2004 | Beard et al. | 560/56 |

FOREIGN PATENT DOCUMENTS

| | | |
|---|---|---|
| WO | WO 93/11755 | 6/1993 |
| WO | WO 97/12853 | 4/1997 |
| WO | WO 01/19770 | 3/2001 |

OTHER PUBLICATIONS

Mangelsdorf et al. (1994) The Retinoid Receptors In: The Retinoids, edited by SPORN et al. p319-349. Raven Press, Ltd., New York.
Okamura et al. Chemistry and Biology of Synthetic Retinoids, CRC Press Inc,. 1990, p324-356.
Mukherjee,R.; Davies, P.J.; Crombie, D.L. Bishoff, E.D.; Cesario, R.M.; Jow Hamann, L.G.; Boehm, M.F.; Mondon, C.E.; Nadzan, A.M.; Paterniti, J.R. Jr.; Heyman, R.A. Sensitization of Diabetic and Obese Mic to Insulin by Retinoid X Receptor Agonists. *Nature* 1997, 386 (6623), 407-410.
J Amer. Chem. Soc. 1940, vol. 62, p. 36, p. 43.
Feigner P.L., Holm M. (1989) Focus, 11:2.
Heyman et al. *Cell* 68, 397-406, (1992).
Allegretto et al. J. Biol. Chem. 268, 26625-26633, 1993.
Cheng et al. Biochemical Pharmacology, v. 22 pp 3099-3108, 1973.

* cited by examiner

*Primary Examiner*—Cecilia J. Tsang
*Assistant Examiner*—Taylor Victor Oh
(74) *Attorney, Agent, or Firm*—Gabor L. Szekeres

(57) ABSTRACT

Diabetic mammals are treated with compounds that are significantly more efficacious as agonists of $RXR_\beta$ retinoid receptors than as agonists of $RXR_\alpha$ or $RXR_\gamma$ retinoid receptors. The treatment reduces serum glucose and triglyceride levels of the mammals without the undesirable side effects of reducing serum thyroxine levels and a transient increase in serum triglyceride levels Compounds suitable for use in the methods of treatments of the present invention are selected by testing and identifying compounds of selective or specific efficacy as agonists of $RXR_\beta$ retinoid receptors in preference over $RXR_\alpha$ and/or $RXR_\gamma$ retinoid receptors. Novel compounds used in the methods of the invention have Formula 1 where the variables are defined as disclosed in the specification.

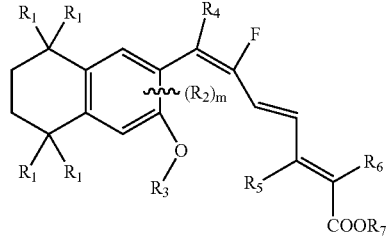

Formula 1

28 Claims, No Drawings

COMPOSITIONS AND METHODS FOR REDUCING SERUM GLUCOSE AND TRIGLYCERIDE LEVELS IN DIABETIC MAMMALS

CROSS-REFERENCE TO RELATED APPLICATION

The present application claims the priority of provisional application Ser. No. 60/443,141, filed on Jan. 28, 2003.

BACKGROUND OF THE INVENTION

1. Field of the Invention

The present invention is in the field of compositions and methods for reducing serum glucose and triglyceride levels in diabetic mammals. More particularly, the present invention relates to treatment of diabetic mammals with compositions containing one or more compounds that are significantly more efficacious as agonists toward $RXR_\beta$ receptors than toward $RXR_\alpha$ and $RXR_\gamma$ retinoid receptors, without the treatment causing a reduction of serum thyroxine levels and transiently raising triglyceride levels. The present invention also relates to novel compounds of selective efficacy as agonists of $RXR_\beta$ receptors and to a method of identifying compounds suitable for reducing serum glucose and/or triglyceride levels in diabetic mammals.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXR_\beta$ and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property.

As is well known in the art of medicinal chemistry, pharmacology and related biological arts efficacy and potency of a drug are related but nevertheless different concepts. As is known the effect of a drug on an enzyme, receptor or other biological test model can be expressed in terms of results accomplished, such as, for example, the percentage of inhibition of an enzyme, or the activity attained on a receptor. $IC_{50}$ numbers express a concentration at which a drug inhibits 50% of the enzyme's activity. $EC_{50}$ numbers express concentration of the drug at which the drugs causes 50% activation of a receptor, the percentage of activity in this case being measured relative to a reference drug or agent which is considered to cause 100% of activity of the receptor. The smaller are the $IC_{50}$ or $EC_{50}$ numbers, thus showing concentrations at 50% activity, the more potent is considered the drug. Unlike potency, efficacy of a drug is not measured by the concentration at which the drug can cause 50% of an effect, but rather on the maximum effect that the drug can bring about at maximum concentration as compared to a standard compound determined to have fall efficacy. Thus, when comparing two drugs, the first one may have a lesser $IC_{50}$ or $EC_{50}$ concentration in a given assay, but the first drug's maximum activity even at maximum concentration may be less than the maximum activity attained by the second drug. In such a case the first drug is considered more potent, but the second one more efficacious. Two drugs may also have substantially equal potency, but substantially different efficacy, and vica versa.

For a general overview of the retinoid receptors see Mangelsdorf et al. (1994) The Retinoid Receptors In: The Retinoids, edited by Sporn et al. p 319–349. Raven Press, Ltd., New York. For another general overview see Dawson and William H. Okamura, Chemistry and Biology of Synthetic Retinoids, published by CRC Press Inc., 1990, pages 324–356. For a disclosure of compounds having some structural relevance to the specific novel compounds utilized in the methods of the present invention see U.S. Pat. No. 5,801,253, and the PCT Publications WO 01/19770 and WO 97/12853.

Relatively recently it has become known that certain retinoid compounds are capable of reducing serum glucose levels in diabetic mammals. Mukherjee, R.; Davies, P. J.; Crombie, D. L. Bishoff, E. D.; Cesario, R. M.; Jow Hamann, L. G.; Boehm, M. F.; Mondon, C. E.; Nadzan, A. M.; Paterniti, J. R. Jr.; Heyman, R. A. Sensitization of Diabetic and Obese Mice to Insulin by Retinoid X Receptor Agonists. *Nature* 1997, 386 (6623), 407–410. The compound (2E,4E, 1'S,2'S)-3-methyl-5-[2'-methyl-2'-(5,5,8,8-tetramethyl-5,6, 7,8-tetrahydro-naphthalen-2-yl)-cyclopropyl]-penta-2,4dienoic acid, described in U.S. Pat. No. 6,114,533, has this property. A disadvantage of the prior art retinoid compounds that reduce serum glucose levels is that their administration usually also results in the pharmacologically undesirable reduction of serum thyroxine levels and a transient increase in serum triglyceride levels. The present invention is directed to novel compounds and methods of identifying them, where the compounds do not have these undesirable side effects.

SUMMARY OF THE INVENTION

The present invention relates to methods of treating diabetic mammals, including humans with compounds that are significantly more efficacious as agonists of $RXR_\beta$ retinoid receptors than as agonists of $RXR_\alpha$ or $RXR_\gamma$ retinoid receptors. The method of treatment in accordance with invention results in significant decrease in serum glucose levels of the diabetic mammals, and also in decrease of triglyceride levels without the undesirable side effects of reducing serum thyroxine levels and a transient increase in serum triglyceride levels.

The present invention also relates to methods of selecting compounds suitable for use in the methods of treatments of the present invention by testing and identifying compounds of selective or specific efficacy as agonists of $RXR_\beta$ retinoid receptors in preference over $RXR_\alpha$ and/or $RXR_\gamma$ retinoid receptors. A compound is considered being specifically or selectively efficacious as agonist of $RXR_\beta$ retinoid receptors when its maximum agonist like activity in one or more assays described below is at least 1.5 times greater for $RXR_\beta$ than for $RXR_\alpha$ and/or for $RXR_\gamma$ retinoid receptors. The present invention also relates to novel compounds used in the methods of the invention, said compounds being disclosed by Formula 1

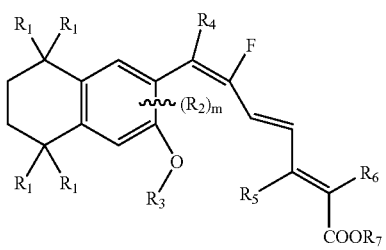

Formula 1 where $R_1$ is H or alkyl of 1 to 6 carbons;
$R_2$ independently is H, alkyl of 1 to 6 carbons, or halogen;
m is an integer having the values 0 to 2;
$R_3$ is alkyl of 1 to 6 carbons;
$R_4$ is alkyl of 1 to 6 carbons;
$R_5$ is H or alkyl of 1 to 6 carbons;.
$R_6$ is H or F, and
$R_7$ is H, alkyl of 1 to 6 carbons, $OCH_2OR_8$ or $OCH_2OCOR_8$ where $R_8$ is alkyl of 1 to 3 carbons, or a pharmaceutically acceptable salt of said compound.

DETAILED DESCRIPTION OF THE INVENTION

General Embodiments and Synthetic Methodology

Definitions

The term alkyl refers to and covers any and all groups which are known as normal alkyl and branched-chain alkyl.

A pharmaceutically acceptable salt may be prepared for any compound in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

The compounds of the present invention include olephinic double bonds about which trans and cis (E and Z) stereoisomerism can exist. The compounds of the present invention have the specific orientations of substituents relative to the double bonds as is indicated in the name of the respective compound, and/or by specific showing in the structural formula of the orientation of the substituents relative to the respective double bonds.

Some of the compounds of the present invention may contain one or more chiral centers and therefore may exist in enantiomeric and diastereomeric forms. The scope of the present invention is intended to cover the trans and cis (E and Z) isomers as specifically shown and/or named, as well as pure enantiomers (optical isomers), diastereomers, mixtures of diastereomers and racemic mixtures of enantiomers.

Reaction Scheme 1 discloses a presently preferred synthetic route to compounds of the invention. Although this synthetic route is general, the cis and/or trans isomerism of the compounds of the invention is indicated properly. Based on the present disclosure and general knowledge in the art those having ordinary skill in synthetic methodology can readily modify the herein described reactions to obtain all compounds within the scope of Formula 1.

Thus, the starting material in Reaction Scheme 1 is a 6-hydroxy-1,2,3,4-tetrahydronaphthalene derivative of Formula 2 which is substituted with the appropriate $R_1$ and $R_2$ groups. Such compounds are readily available in accordance with the chemical patent and scientific literature or can be synthesized by a person of ordinary skill in the art by readily apparent modifications of known synthetic procedures. An example of the starting material of Formula 2 is 3-hydroxy-5,5,8,8-tetramethyl-5,6,7,8-tetrahydronaphthalene which can be prepared as described in *J Amer. Chem. Soc.* 1940, 62, p. 36, p. 43.

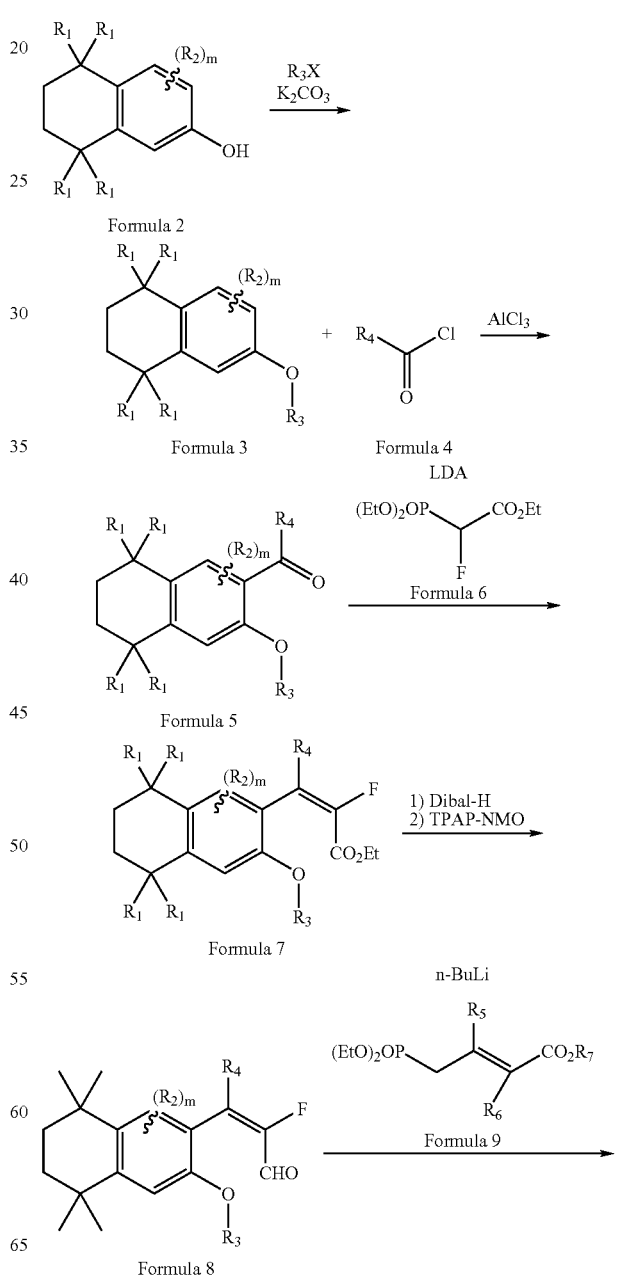

Reaction Scheme 1

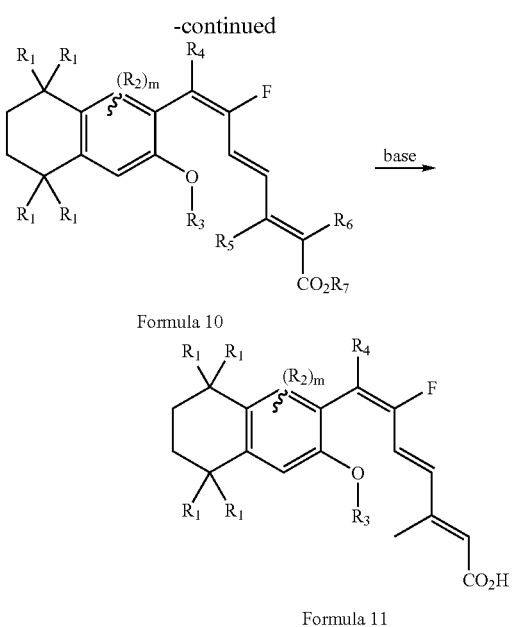

Formula 10

Formula 11

The 3-hydroxy-5,6,7,8-tetrahydronaphthalene derivative of Formula 2 is reacted with an alkylating reagent of the formula $R_3X$ in the presence of base, where $R_3$ is defined as in connection with Formula 1 and X is halogen or other leaving group, preferably iodine. The resulting 3-alkoxy-5,6,7,8-tetrahydronaphthalene derivative of Formula 3 is thereafter subjected to a Friedel Crafts reaction with an acyl chloride of the formula $R_4COCl$ (Formula 4) where $R_4$ is defined as in connection with Formula 1, to provide a 1-(3-alkoxy-5,6,7,8-tetrahydronaphthalen-2-yl)alkan-1-one derivative of Formula 5. Instead of the acyl chloride of Formula 4 another Friedel Crafts reagent capable of introducing the $R_4CO$ group can also be used. The 1-(3-alkoxy-5,6,7,8-tetrahydronaphthalen-2-yl)alkan-1-one derivative of Formula 5 is then subjected to a Horner Emmons reaction with 2-fluoro-triethyl 2-phosphonoacetate (Formula 6) in the presence of lithium diisopropylamide (LDA) to provide and ethyl (E)-3-(3-alkoxy-5,6,7,8-tetrahydronaphthalen-2-yl)-2-fluoropent-2-enoate derivative of Formula 7. The reagent triethyl 2-fluoro-2-phosphonoacetate of Formula 6 is available from Aldrich Chemical Co.

Thereafter the enoate ester of Formula 7 is converted to the corresponding aldehyde (E)-3-(3-alkoxy-5,6,7,8-tetrahydronaphthalen-2-yl)-2-fluoropent-2-enal of Formula 8, first by reduction to the corresponding alcohol by treatment with diisobutylaluminum hydride (Dibal-H), thereafter followed by oxidation to the aldehyde level with tetrapropylammonium peruthenate (TPAP) in the presence of molecular sieves and N-methylmorpholine-N-oxide (NMO). The resulting aldehyde of Formula 8 is subjected to another Horner Emmons reaction with the diethylphosphonate reagent of Formula 9 wherein the variables $R_5$, $R_6$ and $R_7$ are defined as in connection with Formula 1. The reagent of Formula 9 is available in accordance with the chemical patent and scientific literature or can be synthesized by a person of ordinary skill in the art by readily apparent modifications of known synthetic procedures. An example of the reagent of Formula 9 which is utilized for the preparation of the presently preferred compounds of the invention is ethyl 4-(diethoxyphosphoryl)-3-methylbut-2-enoate that can be prepared as described in *JOC*, 1974, 39, 821.

The product of the above-described second Horner Emmons reaction is 7-(3-alkoxy-5,6,7,8-tetrahydronaphthalen-2-yl)-6-fluoro-3-methylnona-2,4,6-trienoate derivative of Formula 10 which is a compound of the invention within the scope of Formula 1. This trienoate ester of Formula 10 is readily saponified by treatment with base to yield a 7-(3-alkoxy-5,6,7,8-tetrahydronaphthalen-2-yl)-6-fluoro-3-methylnona-2,4,6-trienoic acid derivative of Formula 11 which is also a compound of the invention within the scope of Formula 1.

Specific Embodiments of the Compounds of the Invention

Referring now to Formula 1, in the presently preferred compounds of the invention the variable $R_1$ represents alkyl groups of 1 to 3 carbons, and even more preferably methyl groups. The variable $R_2$ is preferably H, an alkyl group of 1 to 3 carbons, or halogen. Even more preferably $R_2$ is H so that the aromatic portion of the tetrahydronaphthlane nucleus is substituted only in the 2-position by the heptanoic acid moiety and in the 3-position by the alkoxy moiety.

The $R_3$ and $R_4$ groups of the preferred compounds of the invention are independently alkyl groups of 1 to 3 carbons. $R_5$ is preferably H or alkyl of 1 to 3 carbons, most preferably methyl and $R_7$ is preferably alkyl of 1 to 3 carbons, H, or a pharmaceutically acceptable salt of the trienoic acid compound wherein $R_7$ is hydrogen.

The synthesis of the presently most preferred compounds of the invention is shown in Reaction Scheme 2, and a detailed description of the experimental procedures for synthesizing these most preferred exemplary compounds is also provided below.

Reaction Scheme 2

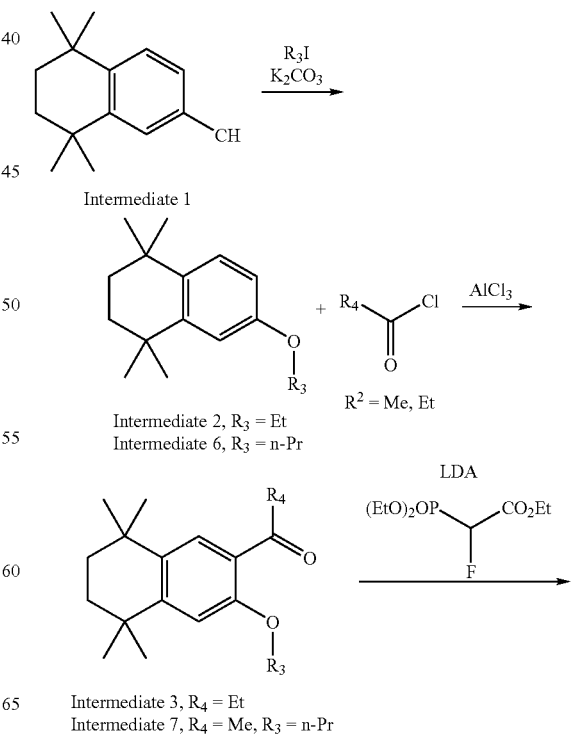

Intermediate 1

Intermediate 2, $R_3$ = Et
Intermediate 6, $R_3$ = n-Pr

Intermediate 3, $R_4$ = Et
Intermediate 7, $R_4$ = Me, $R_3$ = n-Pr

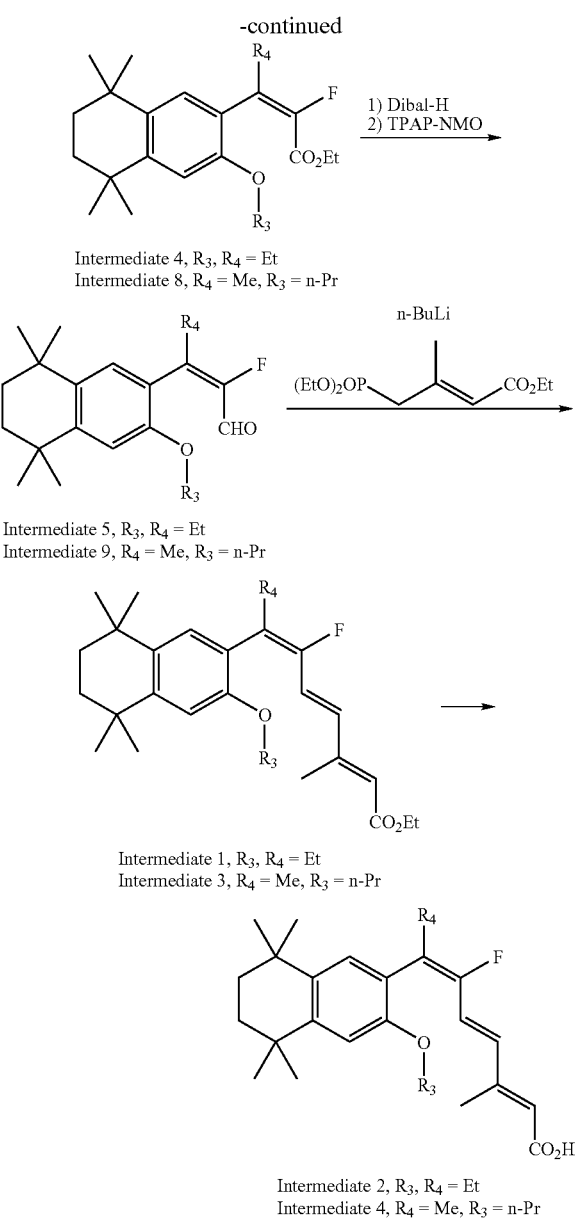

Intermediate 4, R₃, R₄ = Et
Intermediate 8, R₄ = Me, R₃ = n-Pr

Intermediate 5, R₃, R₄ = Et
Intermediate 9, R₄ = Me, R₃ = n-Pr

Intermediate 1, R₃, R₄ = Et
Intermediate 3, R₄ = Me, R₃ = n-Pr

Intermediate 2, R₃, R₄ = Et
Intermediate 4, R₄ = Me, R₃ = n-Pr

Experimental Procedures for Synthesizing the Exemplary Compounds of the Invention 3-Ethoxy-5,5,8,8-tetramethyl-5,6,7,8-tetrahydronaphthalene (Intermediate 2)

Ethyl iodide (10 mL, 124 mmol) was added to a stirring suspension of 6-hydroxy-1,2,3,4-tetrahydronaphthalene (Intermediate 1, 3 g, 14.7 mmol referenced in text potassium carbonate (10 g, 72 mmol), in acetone (100 mL), and the mixture was stirred at reflux for 14 h. The solution was poured into a separatory funnel, water was added, and the products were extracted three times with hexane. The combined organic layers were washed with brine and dried over magnesium sulfate. The solvent was removed in vacuo to give the title compound as a yellow oil.

HNMR (CDCl₃, 300 MHz): δ 1.25 (s, 6H), 1.27 (s, 6H), 1.40 (t, 3H, J=6.5 Hz), 1.66 (s, 4H), 4.00 (q, 2H, J=6.5 Hz), 6.69 (dd, 1H, J=3.9 Hz), 6.83 (d, 1H, J=3 Hz), 7.21 (d, 1H, J=9 Hz).

1-(3-Ethoxy-5,5,8,8-tetramethyl-5,6,7,8-tetrahydronaphthalen-2-yl)propan-1-one (Intermediate 3)

Propionyl chloride (1.44 mL, 16.6 mmol) was added to a stirring solution of 3-ethoxy-5,5,8,8-tetramethyl-5,6,7,8-tetrahydronaphthalene (Intermediate 2, 3.5 g, 15.1 mmol) in dichloromethane (100 mL), and the solution was cooled to 0° C. Aluminum trichloride (2.21 g, 16.6 mmol) was added over two to three minutes, the ice-bath was removed, the yellow solution was stirred for 1 h at room temperature. The solution was poured over ice in a separatory funnel, and the products were extracted three times with ether. The combined organic layers were washed with 10% aqueous sodium hydroxide, brine and dried over magnesium sulfate. The solvent was removed in vacuo to give the title compound as a solid.

HNMR (CDCl₃, 300 MHz): δ 1.16 (t, 3H, J=9Hz), 1.26 (s, 6H), 1.28 (s, 6H), 1.46 (t, 3H, J=6.5 Hz), 1.67 (s, 4H), 3.00 (q, 2H, J=9 Hz), 4.10 (q, 2H, J=6.5 Hz), 6.81 (s, 1H), 7.70 (s, 1H)

Ethyl (E)-3-(3-ethoxy-5,5,8,8-tetramethyl-5,6,7 8-tetrahydronaphthalen-2-yl)-2-fluoropent-2-enoate (Intermediate 4)

Triethyl 2-fluoro-2-phosphonoacetate (8.25 mL, 40.6 mmol referenced in text was added to a stirring solution of lithium diisopropylamide (40.6 mmol) in THF (45 mL) at −78° C. under argon. The dry ice bath was removed for about ten minutes, and then the solution was cooled again to −78° C. A solution of 1-(3-ethoxy-5,5,8,8-tetramethyl-5,6,7,8-tetrahydronaphthalen-2-yl)propan-1-one (Intermediate 3, 3.90 g, 13.5 mmol) and THF (10 mL) was added, and the solution was stirred at 0° C. for 2 h. The reaction was quenched at −78° C. by adding saturated ammonium chloride. The solution was warmed to room temperature and the products extracted three times with ether. The combined organic layers were washed with water, brine and dried over magnesium sulfate. The solvent was removed in vacuo and the residue was purified by silica gel chromatography (96:4, hexane:ethyl acetate) to give the title compound.

HNMR (CDCl₃, 300 MHz): δ 0.86 (t, 3H, J=9 Hz), 1.00 (t, 3H, J=6 Hz), 1.21 (s, 6H), 1.27 (s, 6H), 1.32 (t, 3H, J=6.5 Hz), 1.66 (s, 4H), 2.52 (m, 2H), 3.95 (2 overlapping q, 4H, J=6, 6.5 Hz), 6.73 (s, 1H), 6.84 (s, 1H).

(E)-3-(3-Ethoxy-5,5,8 8-tetramethyl-5,6,7,8-tetrahydronaphthalen-2-yl)-2-fluoropent-2-enol A solution of diisobutylaluminum hydride and hexane (40 mL, 1 M, 40 mmol) was added to a stirring solution of ethyl (E)-3-(3-ethoxy-5,5,8,8-tetramethyl-5,6,7,8-tetrahydronaphthalen-2-yl)-2-fluoropent-2-enoate (Intermediate 4, 3.76 g, 10 mmol) in THF (60 mL) at −78° C. under argon. The solution was stirred at −78° C. for 3 h, and the reaction was quenched at −78° C. by adding methanol. The solution was warmed to room temperature and stirred for 1.5 h. The solution was treated with 1 M aqueous HCl, and the products were extracted three times with ether. The combined organic layers were washed with water, brine and dried over magnesium sulfate. The solvent was removed in vacuo to give the title compound.

HNMR (CDCl$_3$, 300 MHz): δ 0.93 (t, 3H, J=6.5 Hz), 1.23 (s, 6H), 1.27 (s, 6H), 1.36 (t, 3H, J=9 Hz), 1.66 (s, 4H), 2.19 (t, 1H, J=6 Hz), 2.41 (br s, 2H), 3.98 (dt, 2H, J=6, 20 Hz), 4.00 (br s, 2H), 6.77 (s, 1H), 6.95 (s, 1H).

(E)-3-(3-ethoxy-5,5,8,8-tetramethyl-5,6,7,8-tetrahydronaphthalen-2-yl)-2-fluoropent-2-enal (Intermediate 5)

A solution of (E)-3-(3-ethoxy-5,5,8,8-tetramethyl-5,6,7,8-tetrahydronaphthalen-2-yl)-2-fluoropent-2-enol (3.55 g, 8.02 mmol) and dichloromethane (125 mL) in acetonitrile (25 mL) was treated with tetrapropylammonium peruthenate (0.476 g, 1.45 mmol), 4 Å molecular sieves (0.442 g), and N-methylmorpholine-N-oxide (2.78 g, 23.8 mmol), and the mixture was stirred for 0.5 h at ambient temperature. The solution was filtered through a sintered glass funnel containing a bed of silica gel about 1 inch thick using 20% ethyl acetate in hexane as the eluent. The solvent was removed in vacuo to give the title compound.

HNMR (CDCl$_3$, 300 MHz): δ 1.03 (t, 3H, J=6.5 Hz), 1.23 (s, 6H), 1.29 (s, 6H), 1.35 (t, 3H, J=9 Hz), 1.68 (s, 4H), 2.65 (br q, 2H), 4.01 (q, 2H, J=6.5 Hz), 6.78 (s, 1H), 6.97 (s, 1H), 9.13 (d, 1H, J=18 Hz).

Ethyl (2E,4E,6E)-7-(3-ethoxy-5,5,8,8-tetramethyl-5,6,7,8-tetrahydronaphthalen-2-yl)-6-fluoro-3-methyl-nona-2,4,6-trienoate (Compound 1)

A solution of n-butyl lithium and hexane (16.4 mL, 1.6 M, 26.2 mmol) was added over 20 minutes down the side of the flask into a stirring solution of ethyl 4-(diethoxyphosphoryl)-3-methylbut-2-enoate (6.92 g, 26.2 mmol referenced in text in THF (75 mL) and 1,3-dimethyl-3,4,5,6-tetrahydro-2 (1H)-pyrimidinone (DMPU) (1.11 mL, available from Aldrich Chemical Co.) at −78° C. After 30 min, the mixture was treated with a solution of (E)-3-(3-ethoxy-5,5,8,8-tetramethyl-5,6,7,8-tetrahydronaphthalen-2-yl)-2-fluoropent-2-enal (Intermediate 5, 3.55 g, 8.02 mmol) in THF (25 mL). The resulting solution was stirred for 2 h at 0° C. and then cooled again to −78° C. The reaction was quenched at −78° C. by adding saturated aqueous ammonium chloride. The solution was warmed to room temperature, and the products were extracted three times with ether. The combined organic layers were washed with water, brine and dried over magnesium sulfate. The solvent was removed in vacuo to give the title compound after purification by silica gel chromatography using a 94:6 mixture of hexane:ethyl acetate.

HNMR (CDCl$_3$, 300 MHz): δ 0.97 (t, 3H, J=6 Hz), 1.22 (s, 6H), 1.29 (t, 3H, J=6.3 Hz), 1.30 (s, 6H), 1.35 (t, 3H, J=9 Hz), 1.67 (s, 4H), 2.11 (s, 2H), 2.68 (br q, 2H), 4.00 (q, 2H, J=6 Hz), 4.15 (q, 2H, J=6.3 Hz), 5.82 (s, 1H), 6.33 (dd, 1H, J=15, 27 Hz), 6.50 (d, 1H, J=15 Hz), 6.77 (s, 1H), 6.92 (s, 1H).

(2E,4E,6E)-7-(3-Ethoxy-5,5,8,8-tetramethyl-5,6,7,8-tetrahydronaphthalen-2-yl)-6-fluoro-3-methylnona-2,4,6-trienoic acid (Compound 2)

A solution of ethyl (2E,4E,6E)-7-(3-ethoxy-5,5,8,8-tetramethyl-5,6,7,8-tetrahydronaphthalen-2-yl)-6-fluoro-3-methylnona-2,4,6-trienoate (Compound 1, 3.55 g, 8.02 mmol) in ethanol (60 mL) was treated with 2 N aqueous potassium hydroxide (20 mL), and the solution was stirred at 60° C. overnight. The solution was cooled to room temperature, and acidified with 1 N HCl, and the products were extracted three times with ethyl acetate. The combined organic layers were washed with water, brine and dried over magnesium sulfate. The solution was filtered through a sintered glass funnel containing a bed of silica gel about 1 inch thick using ethyl acetate as the eluent. The solvent was removed in vacuo, and the residue was recrystalized form acetonitrile to give the title compound.

HNMR (CDCl$_3$, 300 MHz): δ 0.97 (t, 3H, J=6.5 Hz), 1.22 (s, 6H), 1.29 (s, 6H), 1.35 (t, 3H, J=9 Hz), 1.67 (s, 4H), 2.11 (s, 2H), 2.68 (br q, 2H), 4.00 (q, 2H, J=6.5 Hz), 5.84 (s, 1H), 6.38 (dd, 1H, J=15, 24 Hz), 6.52 (d, 1H, J=15 Hz), 6.77 (s, 1H), 6.92 (s, 1H).

3-n-Propoxy-5,5,8,8-tetramethyl-5,6,7,8-tetrahydronaphthalene (Intermediate 6)

N-Propyl iodide (4.9 mL, 50 mmol) was added to a stirring suspension of 6-hydroxy-1,2,3,4-tetrahydronaphthalene (Intermediate 1, 2.07 g, 10 mmol), potassium carbonate (6.9 g, 50 mmol), in acetone (50 mL), and the mixture was stirred at reflux for 14 h. The solution was poured into a separatory funnel, water was added, and the products were extracted three times with hexane. The combined organic layers were washed with brine and dried over magnesium sulfate. The solvent was removed in vacuo to give the title compound as a yellow oil.

HNMR (CDCl$_3$, 300 MHz): δ 1.03 (t, 3H, J=6.5 Hz), 1.25 (s, 6H), 1.27 (s, 6H), 1.66 (s, 4H), 1.78 (m, 2H, J=6.5 Hz), 3.89 (t, 2H, J=6.5 Hz), 6.70. (dd, 1H, J=3, 6 Hz), 6.83 (d, 1H, J=3 Hz), 7.21 (d, 1H, J=6 Hz).

1-(3-n-Propoxy-5,5,8,8-tetramethyl-5,6,7,8-tetrahydronaphthalen-2-yl)propan-1-one (Intermediate 7)

Acetyl chloride (0.831 g, 11.7 mmol) was added to a stirring solution of 3-n-propoxy-5,5,8,8-tetramethyl-5,6,7,8-tetrahydronaphthalene (Intermediate 6, 2.4 g, 9.7 mmol) in dichloromethane (100 mL), and the solution was cooled to 0° C. Aluminum trichloride (1.56 g, 11.7 mmol) was added over two to three minutes, the ice-bath was removed, the yellow solution was stirred for 1 h at room temperature. The solution was poured over ice in a separatory funnel, and the products were extracted three times with ether. The combined organic layers were washed with 10% aqueous sodium hydroxide, brine and dried over magnesium sulfate. The solvent was removed in vacuo to give the title compound as a solid.

HNMR (CDCl$_3$, 300 MHz): δ 1.07 (t, 3H, J=6.5 Hz), 1.26 (s, 6H), 1.28 (s, 6H), 1.66 (s, 4H), 1.85 (m, 2H, J=6.5 Hz), 2.61 (s, 3H), 3.99 (t, 2H, J=6.5 Hz), 6.81 (s, 1H), 7.73 (s, 1H)

Ethyl (E)-3-(3-n-propoxy-5,5,8,8-tetramethyl-5,6,7,8-tetrahydronaphthalen-2-yl)-2-fluoropent-2-enoate (Intermediate 8)

Triethyl 2-fluoro-2-phosphonoacetate (5.72 mL, 28.1 mmol, was added to a stirring solution of lithium diisopropylamide (28.1 mmol) in THF (54 mL) at −78° C. under argon. The dry ice bath was removed for about ten minutes, and then the solution was cooled again to −78° C. A solution of 1-(3-n-propoxy5,5,8,8-tetramethyl-5,6,7,8-tetrahydronaphthalen-2-yl)propan-1-one (Intermediate 7, 2.70 g, 9.36 mmol) and THF. (10 mL) was added, and the solution was stirred at 0° C. for 2 h. The reaction was quenched at −78° C. by adding saturated ammonium chloride. The solution was warmed to room temperature and the products were extracted three times with ether. The combined organic layers were washed with water, brine and dried over magnesium sulfate. The solvent was removed in vacuo to give the title compound.

HNMR (CDCl$_3$, 300 MHz): δ 0.88 (t, 3H, J=6 Hz), 0.98 (t, 3H, J=6 Hz), 1.22 (s, 6H), 1.28 (s, 6H), 1.66 (s, 4H), 1.72 (t, 3H, J=6.5 Hz), 2.11 (d, 3H, J=3 Hz), 3.87 (t, 2H, J=6 Hz), 3.95 (q, 2H, J=6 Hz), 6.74 (s, 1H), 6.90 (s, 1H).

(E)-3-(3-n-Propoxy-5,5,8,8-tetramethyl-5,6,7,8-tetrahydronaphthalen-2-yl)-2-fluoropent-2-enol A solution of diisobutylaluminum hydride and hexane (40 mL, 1 M, 40 mmol) was added to a stirring solution of ethyl (E)-3-(3-n-propoxy-5,5,8,8-tetramethyl-5,6,7,8-tetrahydronaphthalen-2-yl)-2-fluoropent-2-enoate (Intermediate 8, 3.52 g, 9.36 mmol) in THF (60 mL) at −78° C. under argon. The solution was stirred at −78° C. for 3 h, and the reaction was quenched at −78° C. by adding methanol. The solution was warmed to room temperature and stirred for 1.5 h. The solution was treated with 1 M aqueous HCl, and the products were extracted three times with ether. The combined organic layers were washed with water, brine and dried over magnesium sulfate. The solvent was removed in vacuo to give the title compound after purification by silica gel chromatography (15% ethyl acetate in hexane).

HNMR (CDCl$_3$, 300 MHz): δ 1.01 (t, 3H, J=6.5 Hz), 1.24 (s, 6H), 1.28 (s, 6H), 1.66 (s, 4H), 1.77 (m, 2H, J=6 Hz), 1.98 (d, 3H, J=3 Hz), 3.89 (t, 2H, J=6 Hz), 4.01 (br d, 2H, J=24 Hz), 6.78 (s, 1H), 7.00 (s, 1H).

(E)-3-(3-Propoxy-5,5,8,8-tetramethyl-5,6,7,8-tetrahydronaphthalen-2-yl)-2-fluoropent-2-enal (Intermediate 9)

A solution of (E)-3-(3-propoxy-5,5,8,8-tetramethyl-5,6,7,8-tetrahydronaphthalen-2-yl)-2-fluoropent-2-enol (2.05 g, 6.13 mmol) in dichloromethane (81 mL) and acetonitrile (16 mL) was treated with tetrapropylammonium peruthenate (0.305 g, 0.92 mmol), 4 Å molecular sieves (0.442 g), and N-methylmorpholine-N-oxide (2.41 g, 15.3 mmol), and the solution was stirred for 0.5 h at ambient temperature. The mixture was filtered through a sintered glass funnel containing a bed of silica gel about 1 inch thick using 20% ethyl acetate in hexane as the eluent. The solvent was removed in vacuo to give the title compound.

HNMR (CDCl$_3$, 300 MHz): δ 1.01 (t, 3H, J=6.5 Hz), 1.24 (s, 6H), 1.31 (s, 6H), 1.66 (s, 4H), 1.77 (m, 2H, J=6 Hz), 2.21 (d, 3H, J=3 Hz), 3.93 (t, 2H, J=6 Hz), 6.78 (s, 1H), 7.01 (s, 1H), 9.19 (d, 1H, J=24 Hz).

(2E,4E,6E)-Ethyl 7-(3-propoxy-5,5,8,8-tetramethyl-5,6,7,8-tetrahydronaphthalen-2-yl)-6-fluoro-3-methylnona-2,4,6-trienoate (Compound 3)

A solution of n-butyl lithium and hexane (6.75 mL, 1.6 M, 10.8 mmol) was added over 20 minutes down the side of the flask into a stirring solution of ethyl 4-(diethoxyphosphoryl)-3-methylbut-2-enoate (2.86 g, 10.8 mmol) and THF (40 mL) and 1,3-dimethyl-3,4,5,6-tetrahydro-2(1H)-pyrimidinone (0.70 mL) at −78° C. After 30 min, the solution was treated with a solution of (E)-3-(3-propoxy-5,5,8,8-tetramethyl-5,6,7,8-tetrahydronaphthalen- 2-yl)-2-fluoropent-2-enal (Intermediate 9, 1.80 g, 5.42 mmol) in THF (10 mL). The solution was stirred for 2 h at 0° C. and then cooled again to −78° C. The reaction was quenched at −78° C. by adding saturated aqueous ammonium chloride. The solution was warmed to room temperature, and the products were extracted three times with ether. The combined organic layers were washed with water, brine and dried over magnesium sulfate. The solvent was removed in vacuo to give the title compound after purification by silica gel chromatography using a 94:6 mixture of hexane:ethyl acetate.

HNMR (CDCl$_3$, 300 MHz): δ 1.01 (t, 3H, J=6.5 Hz), 1.23 (s, 6H), 1.28 (t, 3H, J=6.5 Hz), 1.30 (s, 6H), 1.67 (s, 4H), 1.76 (m, 2H, J=6 Hz), 2.11 (s, 3H), 2.12 (s, 3H), 3.89 (t, 2H, J=6 Hz), 4.15 (q, 2H, J=6.5 Hz), 5.83 (s, 1H), 6.42 (dd, 1H, J=15, 24 Hz), 6.50 (d, 1H, J=15 Hz), 6.78 (s, 1H), 6.97 (s, 1H).

(2E,4E,6E)-(E)-7-(3-Propoxy-5,5,8,8-tetramethyl-5,6,7,8-tetrahydronaphthalen-2-yl)-6-fluoro-3-methylnona-2,4,6-trienoic acid (Compound 4)

A solution of ethyl ((2E,4E,6E)-7-(3-propoxy-5,5,8,8-tetramethyl-5,6,7,8-tetrahydronaphthalen-2-yl)-6-fluoro-3-methylnona-2,4,6-trienoate (Compound 3, 2.3 g, 5.20 mmol) in ethanol (40 mL) was treated with 2 N aqueous potassium hydroxide (10 mL), and the solution was stirred at 60° C. overnight. The solution was cooled to room temperature, and acidified with 1 N HCl, and the products were extracted three times with ethyl acetate. The combined organic layers were washed with water, brine and dried over magnesium sulfate. The solution was filtered through a sintered glass funnel containing a bed of silica gel about 1 inch thick using ethyl acetate as the eluent. The solvent was removed in vacuo, and the residue was recrystalized form acetonitrile to give the title compound.

HNMR (CDCl$_3$, 300 MHz): δ 1.01 (t, 3H, J=6.5 Hz), 1.23 (s, 6H), 1.30 (s, 6H), 1.67 (s, 4H), 1.76 (m, 2H, J=6 Hz), 2.13 (s, 6H), 3.90 (t, 2H, J=6 Hz), 5.85 (s, 1H), 6.47 (dd, 1H, J=12, 24 Hz), 6.53 (d, 1H, J=12 Hz), 6.78 (s, 1H), 6.97 (s, 1H).

Biological Activity, Modes of Administration

It has been discovered in accordance with the present invention that compounds which are specifically or selectively afficacious as agonists of RXR$_\beta$ retinoid receptors in preference over RXR$_\alpha$ and RXR$_\gamma$ retinoid receptors are capable of significantly reducing serum glucose levels in diabetic mammals, without the undesirable side effects of also reducing serum thyroxine levels and a transient increase in serum triglyceride levels, and thereby avoid causing undesirable hypothyroidism. A compound is considered specifically or selectively efficacious as agonist of RXR$_\beta$ retinoid receptors if its maximum agonist like activity in one or more assays described below is at least 1.5 times greater for RXR$_\beta$ than for RXR$_\alpha$ and/or RXR$_\gamma$ retinoid receptors. Preferably the maximum agonist like activity of the compound in one or more of the assays described below is at least twice greater, and even more preferably at least 3 times greater for RXR$_\beta$ than for RXR$_\alpha$ and/or RXR$_\gamma$ retinoid receptors.

One such assay is a chimeric receptor transactivation assay which tests for agonist-like activity in the RAR$_\alpha$, RAR$_\beta$ and RAR$_\gamma$ receptor subtypes, and which is based on work published by Feigner P. L. and Holm M. (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay. The results of the ligand binding assay are expressed in $K_i$ numbers. (See Cheng et al. Biochemical Pharmacology Vol. 22 pp 3099–3108, expressly incorporated herein by reference.)

Table 1 discloses the activity of certain exemplary compounds of the invention in the above-described receptor transactivation and binding assays. Particularly, the transactivation data pertaining to activation of the RAR receptors were obtained in the chimeric assay, and the transactivation data pertaining to the activation of RXR receptors were obtained in the holoreceptor assay. In a chimeric receptor transactivation assay the compounds were essentially inactive in activating $RAR_\alpha$, $RAR_\beta$ and $RAR_\gamma$ receptors.

Efficacy in a transactivation assay is expressed as a percentage of the maximum potency attained by the compound compared to a standard which, in this case, is the compound named (2E,4E,1'S,2'S)-3-methyl-5-[2'-methyl-2'-(5,5,8,8-tetramethyl-5,6,7,8-tetrahydro-naphthalen-2-yl)-cyclopropyl]-penta-2,4-dienoic acid. This standard compound is described in U.S. Pat. No. 6,114,533.

In Table 1 NA stands for not active at all as an agonist. ND stands for not determined. The first row of numbers pertaining to each compound is the measured $EC_{50}$ number. The second row of numbers indicates efficacy in percentage as compared to the standard compound, (2E,4E,1'S,2'S)-3-methyl-5-[2'-methyl-2'-(5,5,8,8-tetramethyl-5,6,7,8-tetrahydro-naphthalen-2-yl)-cyclopropyl]-penta-2,4-dienoic acid. The third row of numbers pertaining to each compound is the binding $K_i$ number.

Table 1 shows Compounds 2 and 4 of the invention are significantly more effective in activating the $RXR_\beta$ subtype (RXR is defined as "retinoid X receptor") than in activating $RXR_\alpha$ and $RXR_\gamma$ subtypes. For comparison to the $RXR_\beta$ selective compounds of the invention Table 1 also provides data for the prior art compound (2E,4E,1'S,2'S)-3-methyl-5-[2'-methyl-2'-(5,5,8,8-tetramethyl-5,6,7,8-tetrahydro-naphthalen-2-yl)-cyclopropyl]-penta- 2,4-dienoic acid, that is approximately equally efficacious in activating the $RXR_\alpha$, $RXR_\beta$ and $RXR_\gamma$ subtypes.

As the ensuing data indicate, the selectively $RXR_\beta$ efficacious compounds of the invention not only cause significant decrease in serum glucose levels and of triglyceride levels in diabetic mammals, but in contrast with the prior art standard or reference compound (2E,4E,1'S,2'S)-3-methyl-5-[2'-methyl-2'-(5,5,8,8-tetramethyl-5,6,7,8-tetrahydro-naphthalen-2-yl)-cyclopropyl]-penta-2,4-dienoic acid do not have the undesirable side effect of reducing serum thyroxine levels nor a transient rise in serum triglyceride levels.

The following describes the assays in which the effects of the compounds of the invention were studied in live animals.

TABLE 1

| compound number | Structure | RAR Trans. $EC_{50}$ nM | | | RXR Trans. $EC_{50}$ nM | | |
|---|---|---|---|---|---|---|---|
| | | RAR α | Bind. β | $K_i$ nM γ | RXR α | Bind β | $K_i$ nM γ |
| Standard compound | | NA >10 k | NA >10 k | NA >10 k | 0.08 (100) 1 | 0.4 (100) 1 | 0.09 (100) 1 |
| compound 4 | | NA 590 | 185 (16) 490 | >1 k (15) 720 | NA 6 | 62 (24) 57 | NA ND |
| compound 2 | | 37 (15) 152 | 250 (11) 540 | NA 1510 | 0.8 (17) 22 | 36 (46) 23 | 9 (18) ND |

Description of the Assays

Effects of RXR agonists on serum glucose and triglyceride were studied in diabetic db/db mice. Compound 2 of the invention, an RXR agonist that selectively activates the RXR-beta receptor relative to the RXR-alpha and RXR-gamma receptors, and the standard compound (2E,4E,1'S,2'S)-3-methyl-5-[2'-methyl-2'-(5,5,8,8-tetramethyl-5,6,7,8-tetrahydro-naphthalen-2-yl)-cyclopropyl]-penta-2,4-dienoic acid, an RXR agonist that activates all three RXR-subtypes were compared. Briefly, animals were dosed once daily by oral gavage using corn oil vehicle for a period of 7 consecutive days. Serum samples were collected on day 1 (first day of dosing) and day 7 at hour 0 (immediately prior to dosing) and hour 3 (approximately 3 hours after dosing). Serum glucose and triglyceride levels of these samples were measured as described in the reference manuals: Glucose/HK. Boehringer Mannheim Corporation, 9115 Hague Road, Indianapolis, Ind., USA and Triglycerides/GPO. Roche Diagnostics Corporation, 9115 Hague Road, Indianapolis, Ind., USA, expressly incorporated herein. Only those animals with glucose levels of higher than 300 mg/dl at 0 hour on day 1 were considered as diabetic and included in data analysis.

A measured amount of dosing solution was withdrawn into a metal feeding tube attached to a marked syringe. Animals were restrained by grasping of their back skin while the feeding tube was gently inserted into their mouth and into esophagus. A fixed amount of the dosing solution was displaced into the esophagus/stomach of the animal by pushing the plunger of the syringe. Serum samples were collected from the retro-orbital sinus while the animals were anesthetized. These samples were analyzed by using commercially available kits from Boehringer Manheim for their glucose levels and Roche Diagnostics for their triglyceride levels in a Boehringer Manheim Hatachi Clinical Chemistry Analyzer.

For glucose assay, an enzymatic reaction using hexokinase and glucose-6-phosphodehydrogenase to catalyze glucose to gluconate-6phosphate and NADPH was employed. The amount of NADPH formed during these reactions was equivalent to the amount of glucose in the serum and was measured with a spectrophotometer. For triglycerides, a series of enzymatic reactions which included lipase, glycerol kinase and glycerol phosphate oxidase to formed dihydroacetone phosphate and peroxidase. The peroxidase produced catalyzed a reaction between peroxide and 4-aminophenazone and 4-chlorophenol in a Trinder reaction to generate a color change. This color change was measured by a spectrophotometer and reflected the amount of triglyceride in the sample. Table 2 below shows serum glucose and triglyceride levels obtained in the assay described above.

In another study the efficacy of RXR agonists in the prevention of diabetes was tested in young db/db mice. Animals were dosed orally similarly as described above for 14 days with the standard compound (2E,4E,1'S,2'S)-3-methyl-5-[2'-methyl-2'-(5,5,8,8-tetramethyl-5,6,7,8-tetrahydro-naphthalen-2-yl)-cyclopropyl]-penta-2,4-dienoic acid and Compound 2 of the invention. Serum samples were analyzed by using commercially available kits from Boehring Manheim for their thyroxine (T4) levels in a Boehringer Manheim Hatachi Clinical Chemistry Analyzer as described in the reference manual of Boehringer Mannheim Corporation, 9115 Hague Road, Indianapolis, Ind., USA, expressly incorporated herein. Serum T4 levels for each treatment are shown in Table 3 below.

TABLE 3

| Treatment | Serum thyroxine (µg/dl) |
| --- | --- |
| Vehicle control | 1.61 +/− 0.23* |
| Standard compound, 5 mg/kg | 0.83 +/− 0.29 |
| Compound 2, 50 mg/kg | 1.30 +/− 0.28 |

Mean +/− standard deviation (n = 7).

These results clearly demonstrate that both Compound 2 and the standard or reference compound (2E,4E,1'S,2'S)-3-methyl-5-[2'-methyl-2'-(5,5,8,8-tetramethyl-5,6,7,8-tetrahydro-naphthalen-2-yl)-cyclopropyl]-penta-2,4-dienoic acid are capable of lowering serum glucose in diabetic mouse. However, unlike the reference compound, which induces hypertriglyceridemia and a lowering serum T4 in these animals, Compound 2 of the invention does not affect serum triglyceride and T4 levels. This observation supports the theory that ligands which selectively activate the RXR-beta receptor relative to RXR-alpha and RXR-gamma receptors provide a superior therapeutic profile in the treatment of diabetes when compared to ligands that are not $RXR_\beta$ subtype selective.

Selection of compounds for use in pharmaceutical compositions and methods for treatment of diabetic mammals without the undesirable side effect of reducing serum thyroxine levels is another aspect of the present invention. As it can be seen from the description and results above, this selection is accomplished by assaying compounds in the above-described or similar assays for ability to transactivate the three RXR receptor subtypes, and from these assays identifying agonists having specific or selective efficacy for $RXR_\beta$ receptors and then selecting such agonist as compounds highly suitable for use in the pharmaceutical compositions and methods of treatment of the invention.

TABLE 2

| | Parameter | | | | | | | |
| --- | --- | --- | --- | --- | --- | --- | --- | --- |
| | Glucose (mg/dl) | | | | Triglycerides (mg/dl) | | | |
| Treatment | Day 1, 0 hr | Day 1, 3 hr | Day 7, 0 hr | Day 7, 3 hr | Day 1, 0 hr | Day 1, 3 hr | Day 7, 0 hr | Day 7, 3 hr |
| Vehicle (corn oil) | 516* +/− 67** | 563 +/− 108 | 473 +/− 142 | 485 +/− 130 | 203 +/− 31 | 192 +/− 126 | 220 +/− 78 | 130 +/− 47 |
| AGN 194204 (10 mg/kg) | 501 +/− 87 | 403 +/− 86 | 367 +/− 101 | 301 +/− 40 | 183 +/− 50 | 220 +/− 87 | 137 +/− 32 | 227 +/− 112 |
| AGN 198543 (50 mg/kg) | 529 +/− 123 | 436 +/− 127 | 414 +/− 105 | 350 +/− 140 | 168 +/− 74 | 142 +/− 94 | 157 +/− 106 | 95 +/− 33 |

*mean;
**standard deviation.

Modes of Administration, Dosing

To treat diabetic mammals, including humans for the purpose of reducing serum glucose levels in said mammals a pharmaceutical composition containing one or more compound of the invention is administered to the mammal in daily doses in the range of 1 to 100 mg per kg body weight of the mammal. Preferably the daily dose is between 10 to 50 mg per kg body weight of the mammal.

Generally speaking the compounds of the invention are also useful for preventing or treating diseases and conditions that are responsive to compounds that promote the expression of or bind to receptors belonging to the steroid or thyroid receptor superfamily. More specifically the compounds of the invention can be used for preventing or treating skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. The compounds are also useful for the prevention and treatment of metabolic diseases and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

To treat diabetes the compounds of this invention are preferably administered, orally.

For the prevention or treatment of other diseases or conditions the compounds of the invention may be administered systemically or topically, depending on such considerations as the condition to be treated, need for site-specific treatment, quantity of drug to be administered, and numerous other considerations. Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 1 and 50 mg per kg of body weight per day would be expected to effect a therapeutic result in the treatment of many diseases for which these compounds are useful.

What is claimed is:

1. A compound of the formula

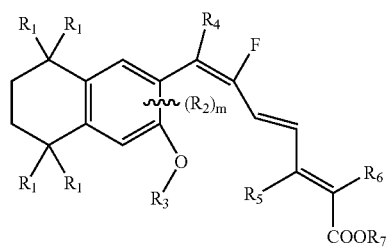

where $R_1$ is H or alkyl of 1 to 6 carbons;
$R_2$ independently is H, alkyl of 1 to 6 carbons, or halogen;
m is an integer having the values 0 to 2;
$R_3$ is alkyl of 1 to 6 carbons;
$R_4$ is alkyl of 1 to 6 carbons;
$R_5$ is H or alkyl of 1 to 6 carbons;
$R_6$ is H or F, and
$R_7$ is H or alkyl of 1 to 6 carbons or a pharmaceutically acceptable salt of said compound.

2. A compound in accordance with claim 1 where $R_1$ is alkyl of 1 to 3 carbons.

3. A compound in accordance with claim 1 where $R_2$ is H, or alkyl of 1 to 3 carbons.

4. A compound in accordance with claim 1 where $R_3$ is alkyl of 1 to 3 carbons and $R_4$ is alkyl of 1 to 3 carbons.

5. A compound in accordance with claim 1 where $R_5$ is H alkyl of 1 to 3 carbons.

6. A compound in accordance with claim 1 where $R_7$ is H, or alkyl of 1 to 3 carbons, or a pharmaceutically acceptable salt of said compound.

7. A compound of the formula

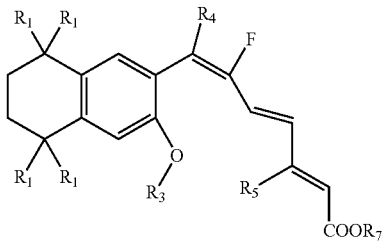

where $R_1$ is alkyl of 1 to 3 carbons;
$R_3$ is alkyl of 1 to 3 carbons;
$R_4$ is alkyl of 1 to 3 carbons;
$R_5$ is H or alkyl of 1 to 3 carbons, and
$R_7$ is H or alkyl of 1 to 6 carbons or a pharmaceutically acceptable salt of said compound.

8. A compound in accordance with claim 7 where $R_7$ is H, alkyl of 1 to 3 carbons, or a pharmaceutically acceptable salt of said compound.

9. A compound in accordance with claim 7 where $R_7$ is H, or a pharmaceutically acceptable salt of said compound.

10. A compound of the formula

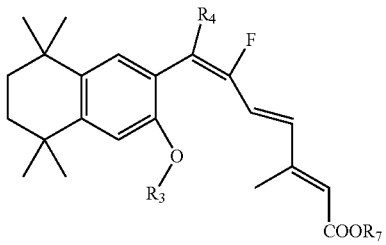

where $R_3$ is ethyl or n-propyl;
$R_4$ is methyl or ethyl, and
$R_7$ is H or alkyl of 1 to 3 carbons or a pharmaceutically acceptable salt of said compound.

11. A compound in accordance with claim 10 where $R_3$ and $R_4$ are ethyl.

12. A compound in accordance with claim 11 where $R_7$ is H or a pharmaceutically acceptable salt of said compound.

13. A compound in accordance with claim 10 where $R_3$ is n-propyl and $R_4$ is methyl.

14. A compound in accordance with claim 13 where $R_7$ is H or a pharmaceutically acceptable salt of said compound.

15. A process for treating a diabetic Type II condition in a mammal comprising administering a compound of the formula to said mammal to reduce the serum glucose level of said mammal

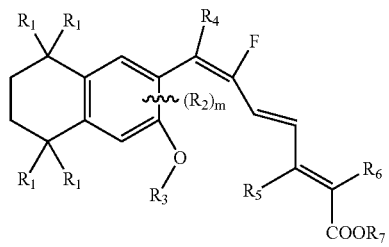

where $R_1$ is H or alkyl of 1 to 6 carbons;
$R_2$ independently is H, alkyl of 1 to 6 carbons, or halogen;
m is an integer having the values 0 to 2;
$R_3$ is alkyl of 1 to 6 carbons;
$R_4$ is alkyl of 1 to 6 carbons;
$R_5$ is H or alkyl of 1 to 6 carbons;
$R_6$ is H or F, and
$R_7$ is H or alkyl of 1 to 6 carbons or a pharmaceutically acceptable salt of said compound and wherein the compound is at least 1.5 times more efficacious as agonist of $RXR_\beta$ retinoid receptors than as agonists of $RXR_\alpha$ or $RXR_\gamma$ retinoid receptors.

16. A process in accordance with claim 15 where the compound administered to the mammal is at least 2.0 times more efficacious as agonist of $RXR_\beta$ retinoid receptors than as agonist of $RXR_\alpha$ or $RXR_\gamma$ retinoid receptors.

17. A process in accordance with claim 15 where the compound administered to the mammal is at least 3 more efficacious as agonist of $RXR_\beta$ retinoid receptors than as agonist of $RXR_\alpha$ or $RXR_\gamma$ retinoid receptors.

18. A process in accordance with claim 15 where the compound has the formula

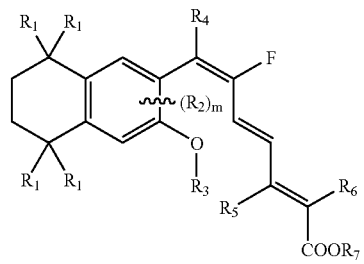

where $R_1$ is H or alkyl of 1 to 6 carbons;
$R_2$ independently is H, alkyl of 1 to 6 carbons, or halogen;
m is an integer having the values 0 to 2;
$R_3$ is alkyl of 1 to 6 carbons;
$R_4$ is alkyl of 1 to 6 carbons;
$R_5$ is H or alkyl of 1 to 6 carbons;
$R_6$ is H or F, and
$R_7$ is H or alkyl of 1 to 6 carbons or a pharmaceutically acceptable salt of said compound.

19. A process in accordance with claim 15 where the compound has the formula

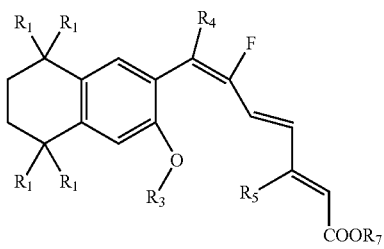

where $R_1$ is alkyl of 1 to 3 carbons;
$R_3$ is alkyl of 1 to 3 carbons;
$R_4$ is alkyl of 1 to 3 carbons;
$R_5$ is H alkyl of 1 to 3 carbons, and
$R_7$ is H or alkyl of 1 to 6 carbons or a pharmaceutically acceptable salt of said compound.

20. A process in accordance with claim 15 where the compound has the formula

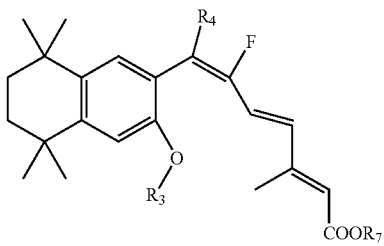

where $R_3$ is ethyl or n-propyl;
$R_4$ is methyl or ethyl, and
$R_7$ is H or alkyl of 1 to 3 carbons or a pharmaceutically acceptable salt of said compound.

21. A process in accordance with claim 20 where in the formula of the compound $R_3$ and $R_4$ are ethyl.

22. A process in accordance with claim 21 where in the formula of the compound $R_7$ is H or a pharmaceutically acceptable salt of said compound.

23. A process in accordance with claim 20 where in the formula of the compound $R_3$ is n-propyl and $R_4$ is methyl.

24. A process in accordance with claim 23 where in the formula of the compound $R_7$ is H or a pharmaceutically acceptable salt of said compound.

25. A process in accordance with claim 15 where administration of the compound to the mammal also reduces serum triglyceride levels without reducing serum thyroxine levels.

26. A method of selecting a compound that is capable of reducing serum glucose level and serum triglyceride level in a mammal having Type II diabetes condition when said compound is administered to the mammal without reducing serum thyroxine level of the mammal, the method comprising the steps of:
assaying several compounds of the formula

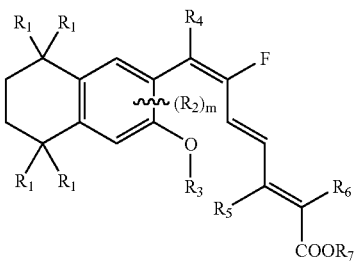

as agonists of $RXR_\alpha$, $RXR_\beta$ and $RXR_\gamma$ retinoid receptors, and identifying the compound that is at least 1.5 times more efficacious as agonist of $RXR_\beta$ retinoid receptors than as agonist of $RXR_\alpha$ or $RXR_\gamma$ retinoid receptors where in the formula of the compound
$R_1$ is H or alkyl of 1 to 6 carbons;
$R_2$ independently is H, alkyl of 1 to 6 carbons, or halogen;
m is an integer having the values 0 to 2;
$R_3$ is alkyl of 1 to 6 carbons;
$R_4$ is alkyl of 1 to 6 carbons;
$R_5$ is H or alkyl of 1 to 6 carbons;
$R_6$ is H or F, and
$R_7$ is H or alkyl of 1 to 6 carbons or a pharmaceutically acceptable salt of said compound.

27. A method in accordance with claim 26 where the identified compound is at least 2.0 times more efficacious as agonist of $RXR_\beta$ retinoid receptors than as agonist of $RXR_\alpha$ or $RXR_\gamma$ retinoid receptors.

28. A method in accordance with claim 26 where the identified compound is at least 3.0 times more efficacious as agonist of $RXR_\beta$ retinoid receptors than as agonist of $RXR_\alpha$ or $RXR_\gamma$ retinoid receptors.

* * * * *